United States Patent
Yamamoto

(10) Patent No.: US 10,123,769 B2
(45) Date of Patent: Nov. 13, 2018

(54) ULTRASOUND DIAGNOSTIC APPARATUS AND DATA PROCESSING METHOD

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 567 days.

(21) Appl. No.: 14/551,558

(22) Filed: Nov. 24, 2014

(65) Prior Publication Data

US 2015/0080731 A1 Mar. 19, 2015

Related U.S. Application Data

(63) Continuation of application No. PCT/JP2013/064485, filed on May 24, 2013.

(30) Foreign Application Priority Data

May 25, 2012 (JP) .................................. 2012-120013

(51) Int. Cl.
*A61B 8/00* (2006.01)
*A61B 8/14* (2006.01)
(Continued)

(52) U.S. Cl.
CPC .............. *A61B 8/14* (2013.01); *A61B 8/5207* (2013.01); *A61B 8/5269* (2013.01); *A61B 8/54* (2013.01);
(Continued)

(58) Field of Classification Search
CPC ............. G01S 7/52046; G01S 7/52047; G01S 15/8997; G01S 15/8915; A61B 8/14;
(Continued)

(56) References Cited

U.S. PATENT DOCUMENTS 4,733,562 A * 3/1988 Saugeon ............... G01S 7/5206
73/626
6,293,912 B1 * 9/2001 Sørensen ............. G10K 11/346
600/437

(Continued)

FOREIGN PATENT DOCUMENTS

JP 2009-142680 A 7/2009

OTHER PUBLICATIONS

International Search Report, issued in PCT/JP2013/064485, dated Jul. 2, 2013.

(Continued)

*Primary Examiner* — Elmer Chao
(74) *Attorney, Agent, or Firm* — Birch, Stewart, Kolasch & Birch, LLP

(57) ABSTRACT

In the ultrasound diagnostic apparatus, the ultrasonic wave transmitter/receiver transmits and receives an ultrasonic beam to a subject to generate reception data; the delay correction unit corrects a delay time of the reception data to align a phase of the reception data; the reception aperture level setting unit sets two or more reception aperture levels of reception data from reception data after correction of the delay time; the image producer produces ultrasound images corresponding to the set reception aperture levels, by performing phase matching addition on the reception data after correction of the delay time; and the image quality determination unit determines image qualities of the ultrasound images corresponding to the set reception aperture levels and selects an ultrasound image having a predetermined image quality.

17 Claims, 7 Drawing Sheets

(51) Int. Cl.
- *G01S 7/52* (2006.01)
- *A61B 8/08* (2006.01)
- *G01S 15/89* (2006.01)

(52) U.S. Cl.
CPC ...... *G01S 7/52046* (2013.01); *G01S 7/52047* (2013.01); *A61B 8/4483* (2013.01); *A61B 8/4488* (2013.01); *A61B 8/461* (2013.01); *A61B 8/58* (2013.01); *A61B 8/585* (2013.01); *G01S 15/8915* (2013.01); *G01S 15/8997* (2013.01)

(58) Field of Classification Search
CPC ... A61B 8/4488; A61B 8/5207; A61B 8/5269; A61B 8/54; A61B 8/58; A61B 8/585; A61B 8/4483; A61B 8/461
See application file for complete search history.

(56) References Cited

U.S. PATENT DOCUMENTS

| | | | | |
|---|---|---|---|---|
| 2010/0022883 | A1* | 1/2010 | Satoh | A61B 8/14 600/447 |
| 2012/0095343 | A1* | 4/2012 | Smith | A61B 8/58 600/447 |
| 2013/0253325 | A1* | 9/2013 | Call | G01S 15/8952 600/447 |

OTHER PUBLICATIONS

International Preliminary Report on Patentability and English translation of the Written Opinion of the International Searching Authority (Forms PCT/IB/338, PCT/IB/373 and PCT/ISA/237), dated Dec. 4, 2014, for International Application No. PCT/JP2013/064485.

* cited by examiner

ULTRASOUND DIAGNOSTIC APPARATUS AND DATA PROCESSING METHOD

CROSS-REFERENCE TO RELATED APPLICATIONS

This application is a Continuation of PCT International Application No. PCT/JP2013/064485 filed on May 24, 2013, which claims priority under 35 U.S.C. § 119(a) to Japanese Application No. 2012-120013 filed on May 25, 2012. Each of the above applications is hereby expressly incorporated by reference, in its entirety, into the present application.

BACKGROUND OF THE INVENTION

The present invention relates to an ultrasound diagnostic apparatus and a data processing method for creating and displaying an ultrasound image of a diagnostic region of a subject using an ultrasonic wave.

An ultrasound diagnostic apparatus using an ultrasound image has hitherto been put into practical use in the field of medicine. In general, the ultrasound diagnostic apparatus has an ultrasound probe in which a transducer array is installed, and an apparatus body connected to the ultrasound probe. In the ultrasound diagnostic apparatus, an ultrasonic beam is transmitted from the ultrasound probe toward a subject, an ultrasonic echo, which is a reflected ultrasonic beam from the subject, is received by the ultrasound probe to acquire a reception signal, and the acquired reception signal is electrically processed by the apparatus body to produce an ultrasound image.

In the conventional ultrasound diagnostic apparatus, the value of the sound speed of ultrasonic wave set for the entire apparatus is fixed to a certain value assuming that the sound speed of ultrasonic wave in the living body of the subject is constant.

However, since the sound speed changes depending on differences in tissues such as a fat layer and a muscular layer in the living body, the sound speed of ultrasonic wave in the subject (hereinafter, referred to as an ambient sound speed) is not uniform. In addition, since the thickness of the fat layer or the muscular layer is different between a fat subject and a thin subject, there are individual differences in the ambient sound speed for each subject.

As described above, in the conventional ultrasound diagnostic apparatus, the sound speed of ultrasonic wave set for the entire apparatus (hereinafter, referred to as a set sound speed) is fixed to a certain value. In this case, the more the ambient sound speed, which is the sound speed in the subject, deviates from the set sound speed, the more the arrival time of the reflected wave (ultrasonic echo) deviates from the delay time set for the ultrasonic wave transmission/reception circuit. For this reason, there has been a problem in that the focusing is degraded, and accordingly, the quality of the obtained ultrasound image is degraded.

In contrast, as shown in FIG. 8, the first embodiment described in JP 2009-142680 A discloses an ultrasound diagnostic apparatus which includes an ultrasonic wave transmitter/receiver 2 that drives a probe 1 to transmit ultrasonic waves to a subject and processes signals of the reflected echo from the subject, a phasing adder 3 that aligns the phases of the reception signals processed by the ultrasonic wave transmitter/receiver 2, and an image display unit 4 that displays the signals from the phasing adder 3 as an image, and in the ultrasound diagnostic apparatus, a plurality of values of switching interval of the optimal reception wave delay correction value are stored in advance in a focus switching interval storage unit 7 for each observation region or each physique of the subject, a focus switching interval instruction unit 8 sets an arbitrary switching interval of reception wave delay correction value in the focus switching interval storage unit 7, and the phasing adder 3 adjusts the focus according to the set switching interval of reception wave delay correction value.

SUMMARY OF THE INVENTION

However, even if a plurality of values of the switching interval of reception wave delay correction value are prepared and appropriately switched as in the focus adjusting method disclosed in JP 2009-142680 A, there has been a problem in that adjustment to the optimal focusing is difficult if the quality of the original reception signal is poor.

The present invention has been made to solve the above-described problems, and it is an object of the present invention to provide an ultrasound diagnostic apparatus and a data processing method capable of adjusting an ultrasound image so as to have the optimal focus even if the quality of the original reception signal of the ultrasound image is poor.

To attain the above object, the present invention provides an ultrasound diagnostic apparatus, comprising:

an ultrasonic wave transmitter/receiver configured to transmit an ultrasonic beam to a subject and receive an ultrasonic echo, which is a reflected ultrasonic beam from the subject, to generate reception data;

a delay correction unit configured to correct a delay time, which is a difference in arrival time of the ultrasonic echo in the reception data, to align a phase of the reception data;

a reception aperture level setting unit configured to set two or more reception aperture levels of reception data which is used when producing an ultrasound image from reception data after correction of the delay time by the delay correction unit;

an image producer configured to produce ultrasound images each corresponding to each of the reception aperture levels set by the reception aperture level setting unit, by performing phase matching addition and predetermined data processing on the reception data after correction of the delay time corresponding to each of the set reception aperture levels; and an image quality determination unit configured to determine image qualities of the ultrasound images each corresponding to each of the set reception aperture levels and select an ultrasound image having a predetermined image quality from among the ultrasound images each corresponding to each of the set reception aperture levels.

Also, the present invention provides a data processing method, comprising steps of:

transmitting an ultrasonic beam to a subject and receiving an ultrasonic echo, which is a reflected ultrasonic beam from the subject, to generate reception data;

correcting a delay time, which is a difference in arrival time of the ultrasonic echo in the reception data, to align a phase of the reception data;

setting two or more reception aperture levels of reception data which is used when producing an ultrasound image from reception data after correction of the delay time;

producing ultrasound images each corresponding to each of the set reception aperture levels by performing phase matching addition and predetermined data processing on the reception data after correction of the delay time corresponding to each of the set reception aperture levels; and determining image qualities of the ultrasound images each corresponding to each of the set reception aperture levels and selecting an ultrasound image having a predetermined image quality from among the ultrasound images each corresponding to each of the set reception aperture levels.

In the present invention, two or more reception aperture levels of reception data which is used when producing an ultrasound image from reception data after delay time correction are set, ultrasound images corresponding to the respective set reception aperture levels are produced from the reception data after delay time correction, and an ultrasound image having a predetermined image quality is selected from among the produced ultrasound images.

Thus, according to the present invention, it is possible to adjust an ultrasound image so as to have the optimal focus even if the quality of the original reception data is poor.

DETAILED DESCRIPTION OF THE INVENTION

Hereinafter, an ultrasound diagnostic apparatus and a data processing method of the present invention will be described in detail based on preferred embodiments shown in the accompanying drawings.

Figure 1:
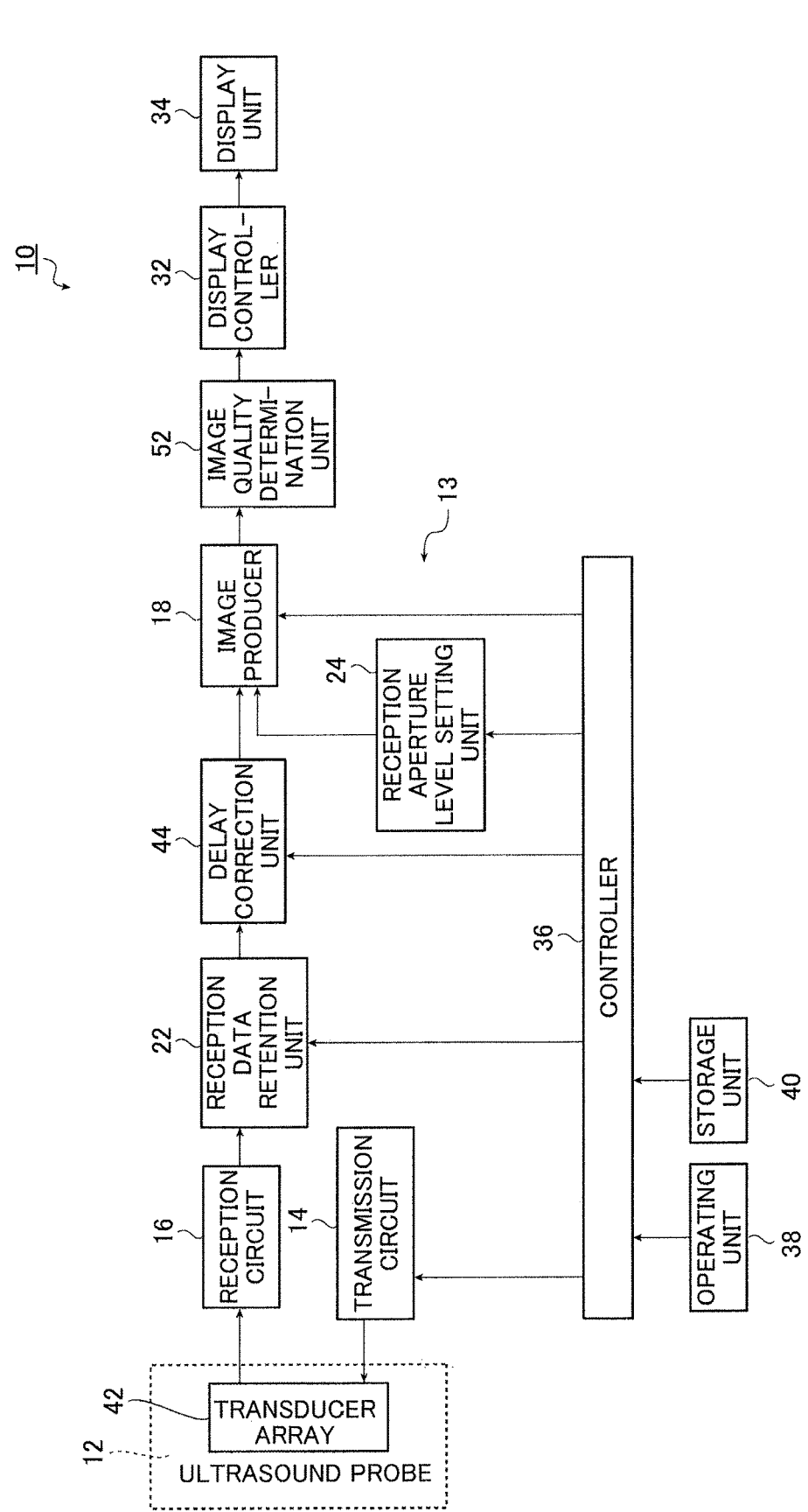
FIG. 1 is a block diagram showing the configuration of an embodiment of an ultrasound diagnostic apparatus for carrying out a data processing method of the present invention.

FIG. 1 is a block diagram showing the configuration of a first embodiment of an ultrasound diagnostic apparatus for carrying out a data processing method of the present invention.

An ultrasound diagnostic apparatus 10 shown in FIG. 1 is configured with an ultrasound probe 12 and an apparatus body 13 connected to the ultrasound probe 12.

The apparatus body 13 includes a transmission circuit 14, a reception circuit 16, a reception data retention unit 22, a delay correction unit 44, a reception aperture level setting unit 24, an image producer 18, an image quality determination unit 52, a display controller 32, a display unit 34, a controller 36, an operating unit 38, and a storage unit 40.

The ultrasound diagnostic apparatus 10 is an apparatus which transmits an ultrasonic beam from the ultrasound probe 12 toward a subject, receives an ultrasonic echo which is a reflected ultrasonic beam from the subject, and produces and displays an ultrasound image from the reception signal of the ultrasonic echo.

The ultrasound probe 12 is used in a state of being brought into contact with a subject, and has a transducer array 42 which is used in a usual ultrasound diagnostic apparatus.

The transducer array 42 has a plurality of ultrasound transducers (ultrasonic wave transmission/reception elements) which are one-dimensionally or two-dimensionally arranged. When an ultrasound image is captured, each of the plurality of ultrasound transducers transmits an ultrasonic beam toward the subject in accordance with a driving signal supplied from the transmission circuit 14, receives an ultrasonic echo from the subject (that is, the ultrasonic beam reflected by the subject), and outputs a reception signal.

Each ultrasound transducer is constituted by a vibrator in which electrodes are formed at both ends of a piezoelectric substance formed of, for example, a piezoelectric ceramic represented by PZT (lead zirconate titanate), a polymer piezoelectric element represented by PVDF (polyvinylidene fluoride), a piezoelectric single crystal represented by PMN-PT (lead magnesium niobate-lead titanate solid solution), or the like.

If a pulsed or continuous-wave voltage is applied across the electrodes of the vibrator, the piezoelectric substance expands and contracts; whereby pulsed or continuous-wave ultrasonic waves are generated from the vibrator, and the generated ultrasonic waves are synthesized to form an ultrasonic beam. When receiving propagating ultrasonic wave, each vibrator expands and contracts to generate an electric signal and the electric signal is output as the reception signal of the ultrasonic wave.

Meanwhile, in the apparatus body 13, the transmission circuit 14 includes a plurality of pulsers, for example. The transmission circuit 14 performs transmission focusing to adjust the amount of delay of each driving signal (timing of applying a driving signal) so that ultrasonic waves transmitted from the plurality of ultrasound transducers of the transducer array 42 form an ultrasonic beam based on the transmission delay pattern selected by the controller 36, and supplies the adjusted driving signals to the plurality of ultrasound transducers. Thus, the ultrasonic beams are transmitted from the plurality of ultrasound transducers to the subject.

The reception circuit 16 amplifies the reception signal supplied from each ultrasound transducer of the transducer array 42, and A/D (analog/digital) converts the amplified reception signal to generate reception data.

The ultrasound probe 12, the transmission circuit 14, and the reception circuit 16 constitute an ultrasonic wave transmitter/receiver in the present invention.

Here, the transmission delay pattern is pattern data of the delay time that is given to a driving signal in order to form an ultrasonic beam in a desired direction with ultrasonic waves transmitted from the plurality of ultrasound transducers. The reception delay pattern is pattern data of the delay time that is given to a reception signal in order to extract an ultrasonic echo from a desired direction with ultrasonic waves received by the plurality of ultrasound transducers.

A plurality of transmission delay patterns and a plurality of reception delay patterns are stored in the storage unit 40 in advance. The controller 36 selects one transmission delay pattern and one reception delay pattern from the plurality of transmission delay patterns and the plurality of reception delay patterns stored in the storage unit 40 and outputs control signals to the transmission circuit 14 and the delay correction unit 44 according to the selected transmission delay pattern and reception delay pattern, thereby performing transmission/reception control of the ultrasonic wave.

Then, the reception data retention unit (a reception data memory) 22 stores the reception data generated by the reception circuit 16 in a sequential manner. In addition, the reception data retention unit 22 stores information regarding the frame rate (for example, parameters indicating the depth of the reflection position of the ultrasonic wave, the density of scanning lines, and the width of a field of vision), which is input from the controller 36, so as to be associated with the reception data described above.

The reception data retained in the reception data retention unit 22 is sequentially read, and is supplied to the delay correction unit 44.

Since the distances between the respective ultrasound transducers and the ultrasonic reflection source in the subject are different, the time taken for the ultrasonic echo to reach each ultrasound transducer is different.

The delay correction unit 44 aligns the phase of the reception data by correcting the difference in arrival time (delay time) of the ultrasonic echo in the reception data of a brightness image supplied from the reception data retention unit 22 based on the reception delay pattern selected by the controller 36.

In the present embodiment, the delay correction unit 44 aligns the phase by delaying the reception data by the difference in arrival time (delay time) of the ultrasonic echo.

In accordance with an instruction input from the operating unit 38 by an operator, which will be described later, the reception aperture level setting unit 24 outputs a reception aperture level setting signal for setting two or more reception aperture (channel) levels of reception data, which is used when the image producer 18 produces an ultrasound image from reception data after delay time correction by the delay correction unit 44, under the control of the controller 36.

Here, the reception aperture means the number of pieces of reception data in the arrangement direction of the ultrasound transducers, which is used when producing an ultrasound image. That is, assuming that the number of ultrasound transducers in the arrangement direction is N, the total number of channels of reception data is N.

Assuming that the reception aperture is n (n is an integer of N or less), in the present embodiment, an ultrasound image is produced by using reception data in the respective ranges of n/2 from the reception data of the channel at the center in the arrangement direction of the ultrasound transducers toward the reception data of the channel at both ends.

Then, the image producer 18 produces an ultrasound image based on the reception data after delay time correction supplied from the delay correction unit 44 and the reception aperture level setting signal supplied from the reception aperture level setting unit 24. That is, the image producer 18 produces an ultrasound images using the reception data after delay time correction each corresponding to each of the reception aperture levels set by the reception aperture level setting unit 24.

Figure 2:
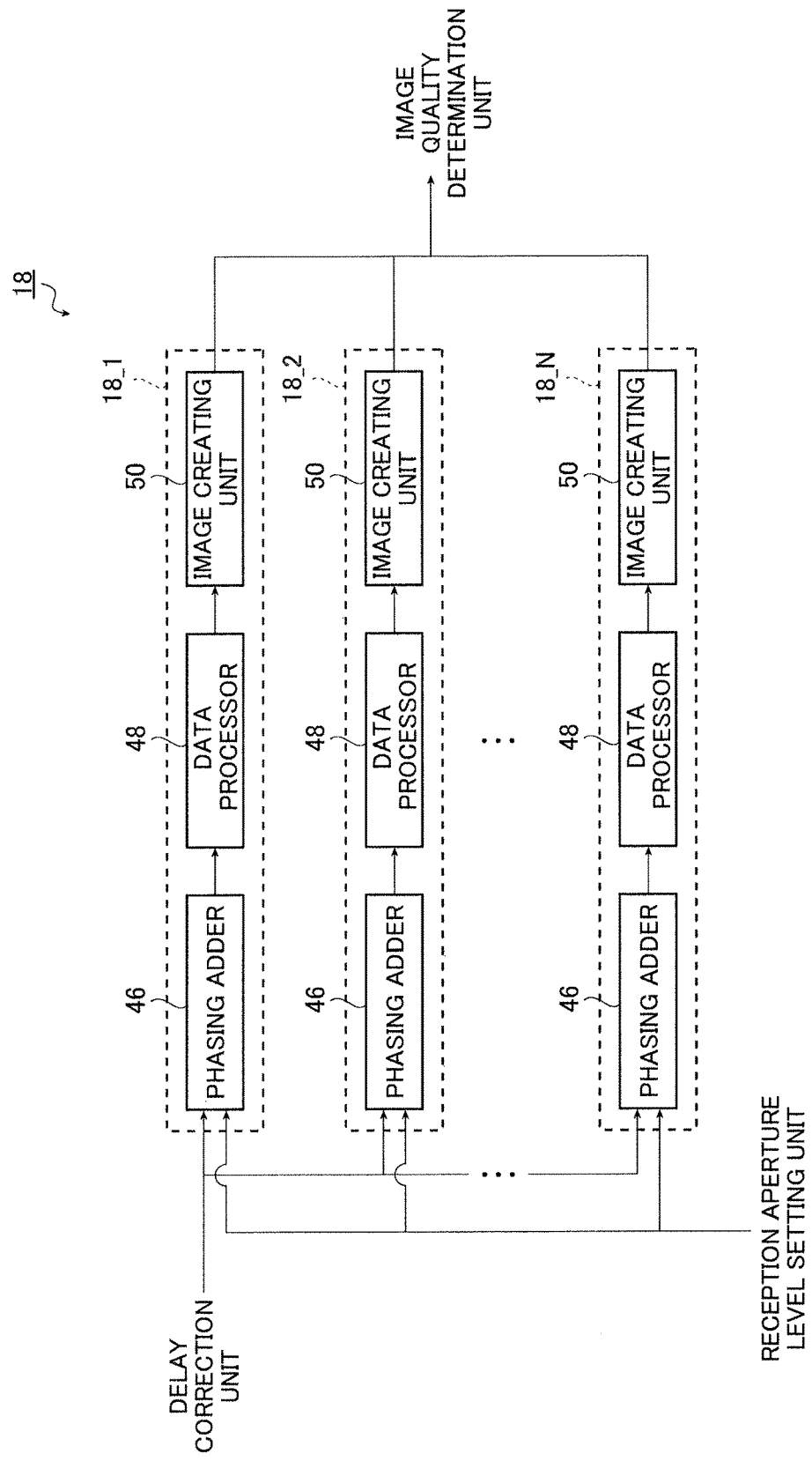
FIG. 2 is a block diagram showing the configuration of an image producer shown in FIG. 1.

As shown in FIG. 2, the image producer 18 includes N image producing units 18_1, 18_2, . . . , and 18_N corresponding to all reception aperture levels 1 to N. In addition, each of the image producing units 18_1, 18_2, . . . , and 18_N includes a phasing adder 46, a data processor 48, and an image creating unit 50.

The image producing units 18_1, 18_2, . . . , and 18_N create ultrasound images corresponding to the reception aperture levels 1 to N, respectively.

In the image producer 18, the image producing unit corresponding to each reception aperture level set by the reception aperture level setting unit 24 creates an ultrasound image corresponding to each set reception aperture level.

The phasing adder 46 performs reception focus processing digitally by performing phase matching addition on the reception data after delay time correction supplied from the delay correction unit 44.

When there is another ultrasonic reflection source at a position different from the position of the ultrasonic reflection source, the arrival time of the reception signal from the other ultrasonic reflection source is different. Therefore, the phase of the reception signal from the other ultrasonic reflection source is cancelled by addition in the phasing adder 46. Thus, the reception signal from the ultrasonic reflection source becomes greatest, thereby becoming in focus. By the reception focus processing, the focus of the ultrasonic echo is narrowed down and reception data (sound ray signal) is generated.

The data processor 48 performs predetermined data processing on the reception data having been subjected to the reception focus processing by the phasing adder 46.

In the present embodiment, the data processor 48 generates a B-mode image signal (image signal of a brightness image in which the amplitude of the ultrasonic echo is expressed by the brightness (luminance) of a point), which is tomographic image information regarding tissue within the subject, by performing correction of attenuation due to the distance depending on the depth of the reflection position of the ultrasonic wave and then performing envelope detection processing.

The generated B-mode image signal is an image signal obtained by a scanning system different from a usual television signal scanning system. Therefore, the data processor 48 converts (raster-converts) the generated B-mode image signal into a usual image signal, for example, an image signal according to the television signal scanning system (for example, an NTSC system).

The image creating unit 50 performs various necessary image processing, such as gradation processing, on the B-mode image signal which has been subjected to the data processing by the data processor 48, and then, creates an ultrasound image corresponding to the B-mode image signal after the image processing.

Then, an image quality determination unit 52 determines the image qualities of the ultrasound images each corresponding to each of the respective reception aperture levels set by the reception aperture level setting unit 24, and selects an ultrasound image having a predetermined image quality from among the ultrasound images corresponding to the respective set reception aperture levels.

The image quality determination unit 52 determines the image quality of each ultrasound image based on the brightness value, sharpness, or the like of the ultrasound image corresponding to each reception aperture level set by the reception aperture level setting unit 24. For example, the image quality determination unit 52 selects an ultrasound image having a value equal to or greater than a threshold value with respect to the brightness value, sharpness, or the like corresponding to an ultrasound image having a predetermined image quality from among the ultrasound images each corresponding to each of the respective reception aperture levels set by the reception aperture level setting unit 24. Alternatively, the image quality determination unit 52 compares the image qualities of all ultrasound images each corresponding to each of the respective reception aperture levels set by the reception aperture level setting unit 24, and selects an ultrasound image having the highest image quality.

Subsequently, the display controller 32 causes the display unit 34 to display the ultrasound image produced by the image producer 18.

The display unit 34 is, for example, a display device such as an LCD, and displays the ultrasound diagnostic image (a video and a still image) and various setting screens under the control of the display controller 32.

The controller 36 controls the respective constituents of the ultrasound diagnostic apparatus 10 on the basis of instructions input from the operating unit 38 by an operator.

The operating unit 38 is an input device for receiving instructions input by the operator, and may be constituted by a keyboard, a mouse, a trackball, a touch panel, or the like.

The storage unit 40 stores an operation program for causing the controller 36 to execute control of the respective constituents of the ultrasound diagnostic apparatus 10, the transmission delay pattern and reception delay pattern, or the like, and may be constituted by a recording medium such as a hard disk, a flexible disk, an MO, an MT, a RAM, a CD-ROM a DVD-ROM, or the like.

The delay correction unit 44, the reception aperture level setting unit 24, the image producer 18, and the display controller 32 are constituted by a CPU (a computer) and an operation program for causing the CPU to execute various processing, but these may be constituted by digital circuits.

Figure 3:
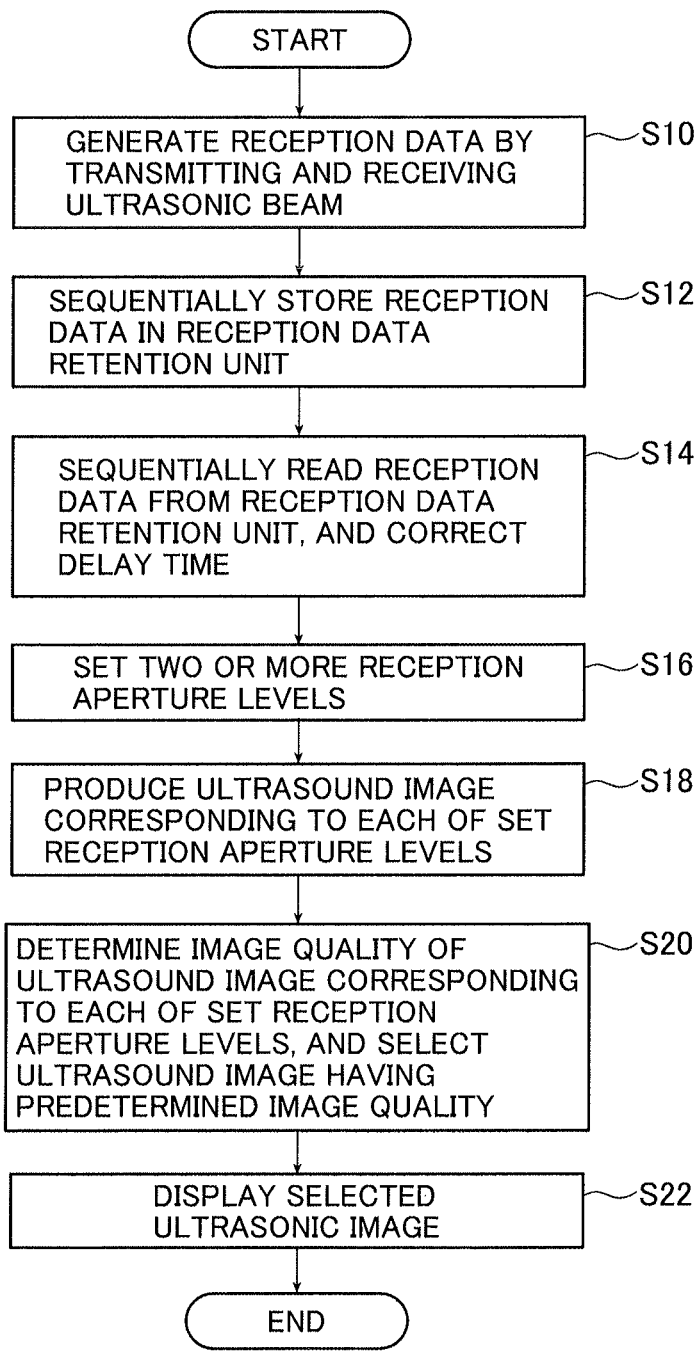
FIG. 3 is a flowchart showing the flow of the process in the ultrasound diagnostic apparatus shown in FIG. 1.
Figure 4:
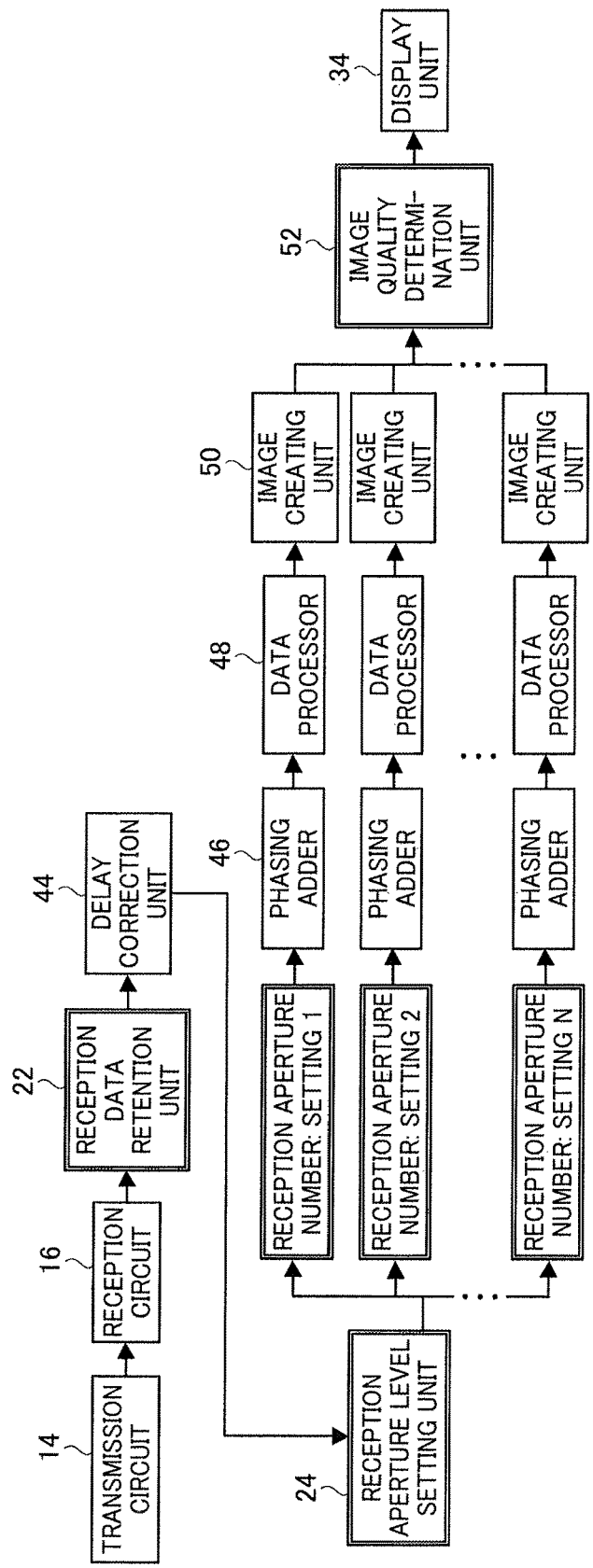
FIG. 4 is a conceptual diagram showing the flow of the process in the ultrasound diagnostic apparatus shown in FIG. 1.

Next, the operation of the ultrasound diagnostic apparatus 10 will be described with reference to the flowchart shown in FIG. 3 and the conceptual diagram shown in FIG. 4. FIG. 3 is a flowchart showing the flow of the process in the ultrasound diagnostic apparatus shown in FIG. 1, and FIG. 4 is a conceptual diagram showing the flow of the process.

An ultrasound probe 12 is brought into contact with a subject, and an instruction of an operator is input from the operating unit 38 to start ultrasound diagnosis.

When the ultrasound diagnosis is started, the controller 36 sets a transmission direction of the ultrasonic beam and a reception direction of the ultrasonic echo for each ultrasound transducer, and selects a transmission delay pattern according to the transmission direction of the ultrasonic beam and selects a reception delay pattern according to the reception direction of the ultrasonic echo. Then, the controller 36 outputs control signals to the transmission circuit 14 and the delay correction unit 44 according to the selected transmission delay pattern and the selected reception delay pattern, thereby performing transmission/reception control of the ultrasonic wave.

In response to this, in the transmission circuit 14, a transmission focus of the driving signal of each ultrasound transducer is performed based on the selected transmission delay pattern, and the ultrasonic beams are transmitted from the plurality of ultrasound transducers to a subject.

Then, the ultrasonic echo from the subject is received by the plurality of ultrasound transducers, and the reception signals are output from the plurality of ultrasound transducers.

The reception circuit 16 generates reception data by amplifying the reception signal supplied from each ultrasound transducer and performing A/D conversion of the amplified signal (step S10).

The reception data generated by the reception circuit 16 is sequentially stored in the reception data retention unit 22 (step S12).

Then, the reception data stored in the reception data retention unit 22 is sequentially read, and is supplied to the delay correction unit 44.

The delay correction unit 44 aligns the phase by correcting the delay time of the reception data supplied from the reception data retention unit 22 based on the selected reception delay pattern (step S14).

Meanwhile, in accordance with an instruction input from the operating unit 38 by the operator, the reception aperture level setting unit 24 outputs a reception aperture level setting signal for setting two or more reception aperture levels, which is used when the image producer 18 produces an ultrasound image, under the control of the controller 36 (step S16).

Here, the same result is obtained regardless of the order of the timing for setting the reception aperture levels of the reception data and the timing for correcting the delay time of the reception data. However, as in the present embodiment, it is preferable to perform the delay time correction of the reception data first because the processing of delay time correction is performed only once. In contrast, in the case where the setting of the level of reception aperture of the reception data is performed first, the delay time correction of the reception data has to be performed in each image processing unit, for example.

The image producer 18 produces an ultrasound image based on the reception data after delay time correction supplied from the delay correction unit 44 and the reception aperture level setting signal supplied from the reception aperture level setting unit 24.

In the image producer 18, the image producing unit corresponding to each reception aperture level set by the reception aperture level setting signal produces an ultrasound image corresponding to each set reception aperture level (step S18).

That is, in the image producing unit corresponding to each set reception aperture level, the phasing adder 46 digitally performs reception focus processing on the reception data after delay time correction, thereby generating reception data in which the focus of the ultrasonic echo is narrowed down.

Then, the data processor 48 generates a B-mode image signal by performing data processing on the reception data which has been subjected to the reception focus processing, and the image creating unit 50 creates an ultrasound image from the B-mode image signal. Thus, the ultrasound image corresponding to each reception aperture level set by the reception aperture level setting signal is created.

Then, the image quality determination unit 52 determines the image qualities of the ultrasound images corresponding to the respective set reception aperture levels, and selects an ultrasound image having a predetermined image quality, for example, an ultrasound image having the highest image quality (step S20).

Finally, the ultrasound image produced by the image producer 18 is displayed on the display unit 34 under the control of the display controller 32 (step S22).

It is not essential to provide the reception data retention unit 22. Even if the reception data is not retained, it is possible to produce ultrasound images corresponding to the respective set reception aperture levels. In this case, for example, a plurality of image processing units that perform phasing addition with reception aperture levels determined in advance are prepared, the reception data produced by the reception circuit 16 is divided, and the pieces of data divided are respectively supplied to the image processing units corresponding to the respective differently set reception aperture levels, thereby producing ultrasound images.

In general, reception data at the center in the arrangement direction of ultrasound transducers has a larger signal strength than that of reception data at both ends in the arrangement direction, and accordingly, the signal/noise (S/N) ratio of the reception data at the center in the arrangement direction is better than that at both ends in the arrangement direction.

Therefore, when the phasing adder 46 performs phase matching addition on the reception data after delay time correction supplied from the delay corrector 44, the reception aperture is made narrow if the S/N ratio of the reception data at both ends is poor. Thus, it is possible to obtain the reception data having a good S/N ratio by performing phase matching addition in a state where the reception data at both ends is excluded. However, if the reception aperture is made narrow, the weight of each piece of reception data before phase matching addition becomes large. Accordingly, for example, if a certain piece of reception data has noise, reception data after phase matching addition is greatly influenced by the noise.

As described above, the reception aperture for adjusting the ultrasound image so as to have the optimal focus differs depending on the quality of the original reception data or reception signal.

For example, in the case of point reflection in which the ultrasonic reflection source is isolated, a possibility that the reception data will have little noise is high. Therefore, in this case, it is thought that reducing the reception aperture is preferable. In contrast, in the case where point reflections are densely present as the ultrasonic reflection source such as a calcified portion of breast cancer, a possibility that the reception data will have noise is high. Therefore, in this case, it is thought that increasing the reception aperture is preferable.

Therefore, according to the ultrasound diagnostic apparatus 10 of the present embodiment, even if the quality of the original reception data or image signal is poor, it is possible to adjust the ultrasound image so as to have the optimal focus by providing the image producing units 18_1, 18_2, . . . , and 18_N corresponding to all levels 1 to N of reception aperture, setting two or more reception aperture levels, creating ultrasound images using the image producing units corresponding to the set reception aperture levels, and selecting an ultrasound image having a predetermined image quality from among the created ultrasound images by the image quality determination unit 52.

Figure 5:
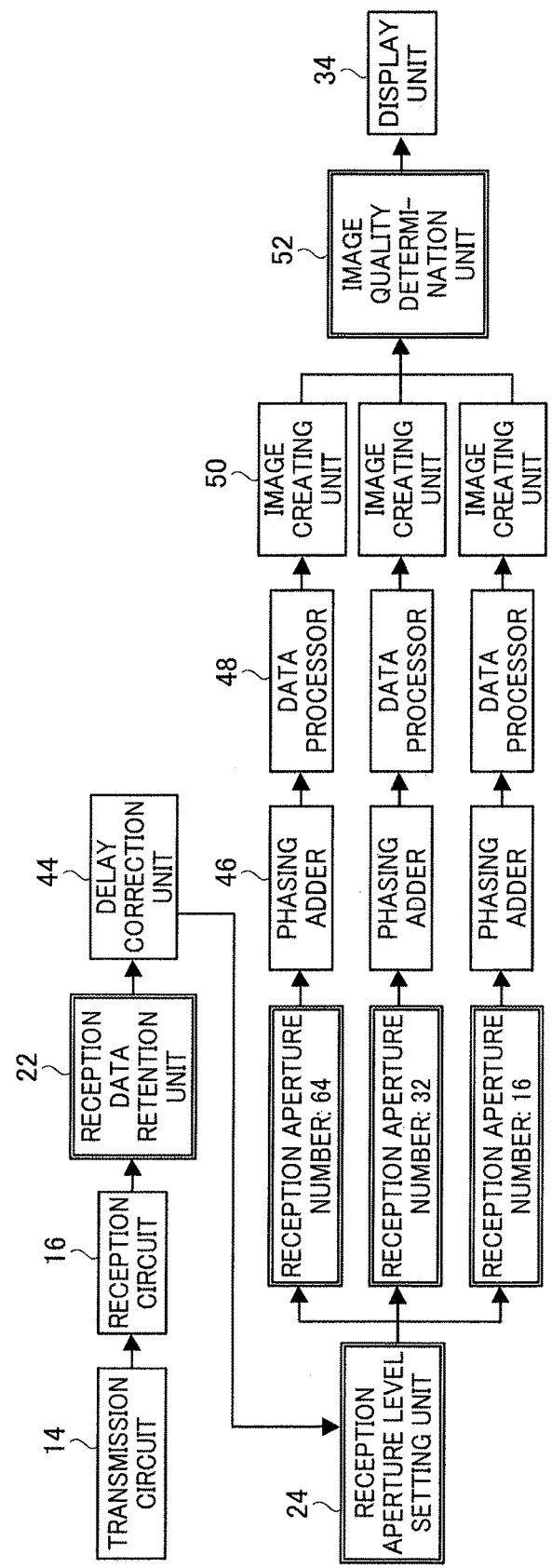
FIG. 5 is a conceptual diagram of an embodiment showing the flow of the process in the ultrasound diagnostic apparatus shown in FIG. 1.

Next, an example of the case where the total number of channels of reception data is N=64 and three reception aperture levels n1=64, n2=32, and n3=16 are set will be described with reference to the conceptual diagram shown in FIG. 5. FIG. 5 is a conceptual diagram of ad embodiment showing the flow of the process in the ultrasound diagnostic apparatus shown in FIG. 1.

In the present embodiment, as shown in FIG. 5, the reception aperture level setting unit 24 sets three reception aperture levels n1=64, n2=32, and n3=16. In response to this, in the image producer 18, ultrasound images corresponding to the set three reception aperture levels n1=64, n2=32, and n3=16 are created by image producing units 18_64, 18_32, and 18_16 corresponding to the three reception aperture levels n1=64, n2=32, and n3=16 set by the reception aperture level setting unit 24.

Then, the image quality determination unit 52 determines the image qualities of the ultrasound images corresponding to the three reception aperture levels n1=64, n2=32, and n3=16, and selects an ultrasound image having a predetermined image quality, for example, an ultrasound image having the highest image quality.

Figure 6A:
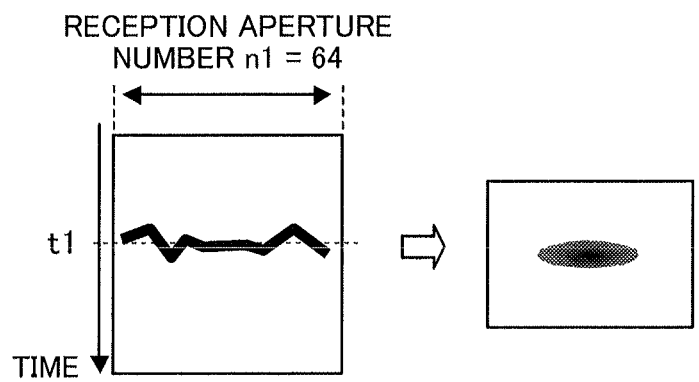
FIGS. 6A, 6B, and 6C are conceptual diagrams respectively showing the states of three pieces of reception data after delay time correction corresponding to the three reception aperture levels n1=64, n2=32, and n3=16 and the ultrasound images (brightness images) thereof.
Figure 6B:
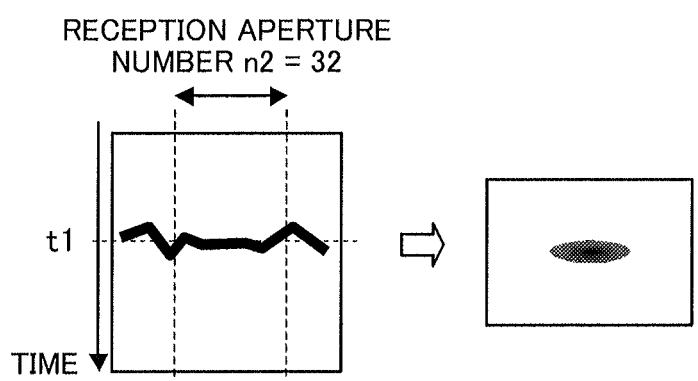
Figure 6C:
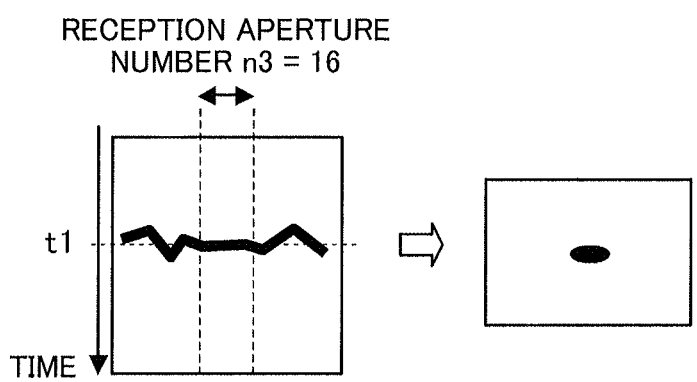

FIGS. 6A, 6B, and 6C are conceptual diagrams showing the states of three pieces of reception data after delay time correction corresponding to the three reception aperture levels n1=64, n2=32, and n3=16 and their ultrasound images (brightness images), respectively.

For example, as shown in FIG. 6A, when the reception aperture level is n1=64, an ultrasound image is created using the reception data of all channels N=64. The graph on the left side in FIG. 6A shows the state of the reception data after delay time correction, where the horizontal axis indicates the arrangement direction of channels of the reception data (arrangement direction of a plurality of ultrasound transducers), and the vertical axis indicates time. The graph on the right side in FIG. 6A shows an ultrasound image corresponding to the reception data at time t1 of the graph on the left side in FIG. 6A.

The reception data shown in the graph in FIG. 6A is reception data after delay time correction, and the S/N ratio of the reception data at both ends is poor since the signal strength at both ends is weak as described above. When the reception aperture level is n1=64, the image producing unit creates an ultrasound image using the reception data of all channels. Therefore, when performing phase matching addition at time t1, a component having a phase shifted due to the influence of noise of the reception data at both ends is also added. As a result, the brightness value is reduced.

On the other hand, as shown in FIG. 6B, when the reception aperture level is n2=32, an ultrasound image is produced using the reception data of the channel of n2=32 at the center in the arrangement direction of ultrasound transducers. In this case, the influence of noise of the reception data at both ends is reduced. Accordingly, when performing phase matching addition, the influence of a component having a shifted phase of the reception data at both ends is reduced. As a result, it is possible to obtain a high-brightness ultrasound image, compared with the case of the reception aperture level n1=64.

The case of the reception aperture level n3=16 shown in FIG. 6C is also the same as the case of the reception aperture level n2=32.

Figure 7:
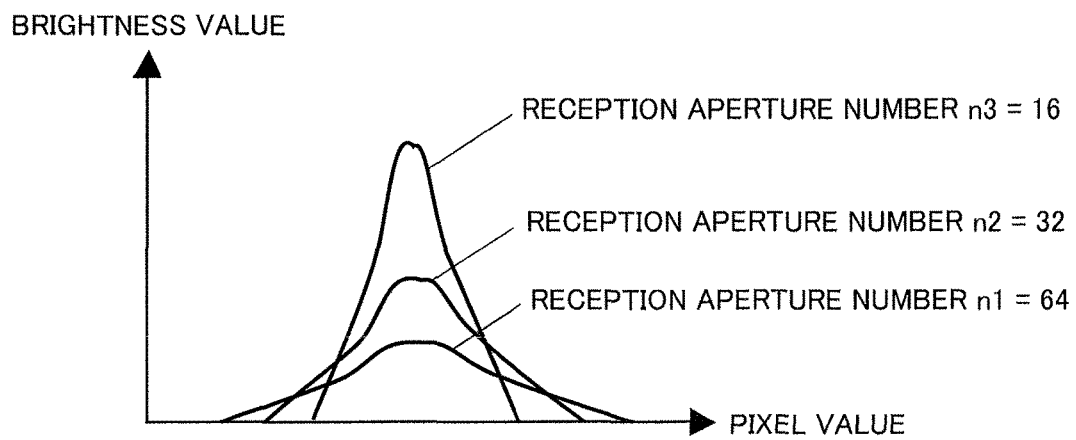
FIG. 7 is a graph showing the state of the cross section of each of ultrasound images at time t1 corresponding to the three reception aperture levels n1=64, n2=32, and n3=16.
Figure 8:
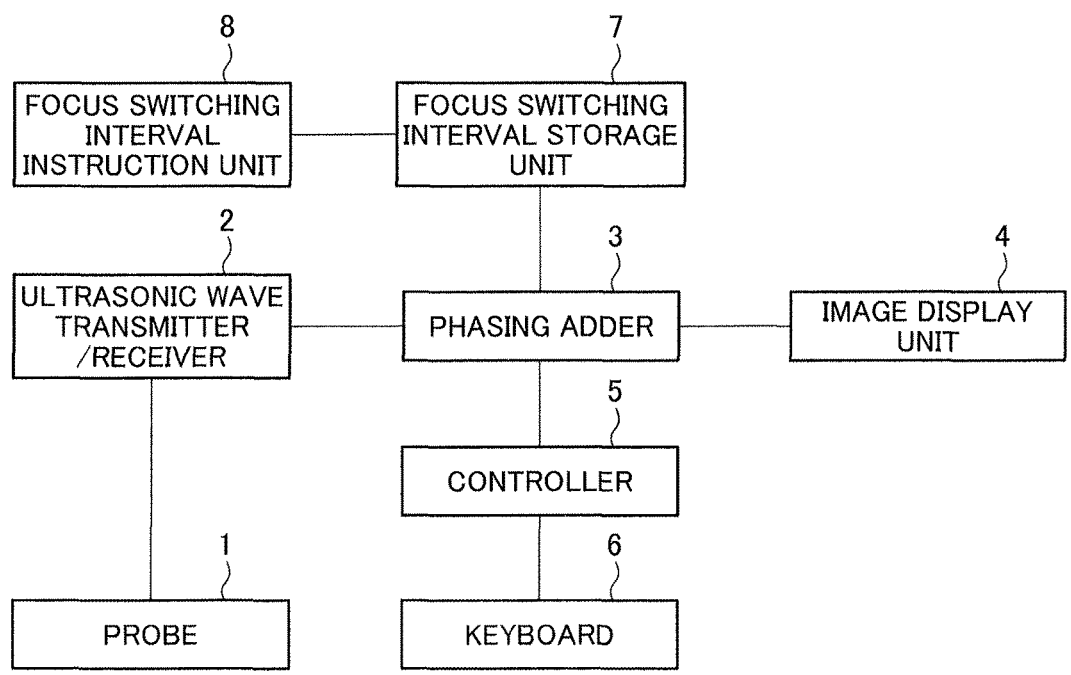
FIG. 8 is a block diagram showing the configuration of an ultrasound diagnostic apparatus disclosed in JP 2009-142680 A.

Finally, FIG. 7 is a graph showing the state of the cross section of each of ultrasound images at time t1 corresponding to the three reception aperture levels n1=64, n2=32, and n3=16. The horizontal axis of the graph indicates a pixel value, and the vertical axis of the graph indicates a brightness value.

As shown in the graph, referring to the state of the cross section of each of the ultrasound images at time t1 corresponding to the three reception aperture levels n1=64, n2=32, and n3=16, the brightness value becomes higher and the sharpness becomes larger (the width of the pixel value becomes smaller) in the order of reception aperture level n1=64, n2=32, and n3=16.

The image quality determination unit 52 determines the image quality of each of the ultrasound images based on the brightness value, sharpness, or the like of the cross section of each of the ultrasound images at time t1 corresponding to the three reception aperture levels n1=64, n2=32, and n3=16.

In the present embodiment, the image quality determination unit 52 determines that the ultrasound image corresponding to the reception aperture level n3=16 is an image having the highest image quality, for example.

In the embodiment described above, the image producer 18 includes a plurality of image producing units that produce ultrasound images corresponding to all reception aperture levels 1 to N, and produces ultrasound images each corresponding to each of the reception aperture levels set by the reception aperture level setting unit 24 in parallel using two or more image producing units corresponding to the set reception aperture levels simultaneously. Thus, it is possible to shorten the processing time by parallel processing using a plurality of image producing units.

In contrast, the image producer 18 may have a single image producing unit that produces an ultrasound image from the reception data. In this case, ultrasound images each corresponding to each of the reception aperture levels set by the reception aperture level setting unit 24 can be sequentially produced by using one image producing unit in a time-division manner. Thus, by using one image producing unit in a time-division manner, it is possible to reduce the circuit size and the apparatus cost.

In addition, when one image producing unit is used in a time-division manner, the image quality determination unit 52 may sequentially determine the image qualities of ultrasound images corresponding to the reception aperture levels 1 to N, stop the determination of the image quality of each ultrasound image when an ultrasound image having a value equal to or greater than a threshold value with respect to the brightness value, sharpness, or the like corresponding to an ultrasound image having a predetermined image quality is detected, and select the detected ultrasound image as an ultrasound image having a predetermined image quality. Thus, it is possible to reduce the time required for the determination of image quality.

The present invention is basically as described above.

Hereinbefore, the present invention has been described in detail, but needless to say, the present invention is not limited to the above-described embodiments, and may be improved or modified in various ways within a scope that does not depart from the gist of the present invention.

What is claimed is:

1. An ultrasound diagnostic apparatus, comprising:
   an ultrasonic wave transmitter/receiver configured to transmit an ultrasonic beam to a subject and receive an ultrasonic echo, which is a reflected ultrasonic beam from the subject, to generate reception data;
   a processor configured to correct a delay time, which is a difference in arrival time of the ultrasonic echo in the reception data, to align a phase of the reception data;
   the processor further configured to set two or more reception aperture levels of reception data which is used when producing an ultrasound image from reception data after correction of the delay time by the delay correction unit;
   the processor further configured to produce ultrasound images, the ultrasound images including an image for each of the corresponding reception aperture levels, by performing phase matching addition and a first data processing including at least one of correction of attenuation and gradation processing on the reception data after correction of the delay time corresponding to each of the set reception aperture levels; and
   the processor further configured to determine image qualities of the ultrasound images, the ultrasound images including an image for each of the corresponding set reception aperture levels and to select at least a first ultrasound image having an image quality equal to or greater than a first image quality from among the ultrasound images corresponding to the respective set reception aperture levels, the image quality including one of brightness, sharpness, or an index related to signal/noise.

2. The ultrasound diagnostic apparatus according to claim 1, further comprising a reception data retention memory configured to retain the reception data generated by the ultrasonic wave transmitter/receiver,
   wherein the processor is further configured to correct a delay time of reception data supplied from the reception data retention unit to align the phase of the reception data.

3. The ultrasound diagnostic apparatus according to claim 1,
   wherein the processor is further configured to align the phase by delaying the reception data corresponding to each of a plurality of ultrasonic wave transmission/reception elements included in the ultrasonic wave transmitter/receiver by an amount corresponding to the delay time.

4. The ultrasound diagnostic apparatus according to claim 1,
   wherein the processor further controls a plurality of image producing units in parallel, each of the plurality of image producing units configured to produce an ultrasound image corresponding to each of the set reception aperture levels by performing the phase matching addition and the first image processing, the processor configured to produce the ultrasound images simultaneously.

5. The ultrasound diagnostic apparatus according to claim 1,
   wherein the processor controls one image producing unit and is configured to produce an ultrasound image corresponding to each of the set reception aperture levels by performing phase matching addition and the first image processing, the processor configured to produce the ultrasound images simultaneously.

6. The ultrasound diagnostic apparatus according to claim 1,
   wherein, assuming that a number of ultrasonic wave transmission/reception elements included in the ultrasonic wave transmitter/receiver in an arrangement direction is N and that the reception aperture is n (n is an integer of N or less), the processor produces an ultrasound image by using reception data in a respective range of n/2 channels of data from the reception data of the ultrasonic wave transmission/reception element of a channel at a center in the arrangement direction of the ultrasonic wave transmission/reception elements toward the reception data of the ultrasonic wave transmission/reception element of channel at both ends of ultrasonic wave transmitter/receiver.

7. The ultrasound diagnostic apparatus according to claim 1,
   wherein the processor further controls:
   a phasing adder configured to perform reception focus processing by performing phase matching addition on the reception data after delay time correction;
   a data processor configured to perform the first data processing on the reception data having been subjected to the reception focus processing by the phasing adder; and
   an image creating unit configured to perform image processing on the reception data which has been subjected to the data processing by the data processor, and then, create an ultrasound image corresponding to the reception data after the image processing.

8. The ultrasound diagnostic apparatus according to claim 7,
wherein the first data processing includes correction of attenuation due to the distance depending on the depth of the reflection position of the ultrasonic wave and envelope detection processing.

9. The ultrasound diagnostic apparatus according to claim 1,
wherein the processor is further configured to determine the image quality of the ultrasound image based on a brightness value of the ultrasound image produced.

10. The ultrasound diagnostic apparatus according to claim 1,
wherein the processor is further configured to determine the image quality of the ultrasound image based on sharpness of the ultrasound image produced.

11. The ultrasound diagnostic apparatus according to claim 1, further comprising:
a storage having a plurality of transmission delay patterns which are pattern data of the delay time that is given to driving signals of a plurality of ultrasonic wave transmission/reception elements included in the ultrasonic wave transmitter/receiver in order to form the ultrasonic beam in a desired direction with ultrasonic waves transmitted from the plurality of ultrasonic wave transmission/reception elements, and a plurality of reception delay patterns which are pattern data of the delay time that is given to a reception signal of the ultrasonic echo in order to extract the ultrasonic echo from a desired direction with ultrasonic waves received by the plurality of ultrasonic wave transmission/reception elements; and
the processor is further configured to select one transmission delay pattern and one reception delay pattern from the plurality of transmission delay patterns and the plurality of reception delay patterns stored in the storage and perform transmission/reception control of the ultrasonic wave according to the selected transmission delay pattern and reception delay pattern;
wherein the ultrasonic wave transmitter/receiver performs transmission focusing to adjust the amount of delay of the driving signals of the plurality of ultrasonic wave transmission/reception elements based on the transmission delay pattern selected by the processor, and transmits the ultrasonic beams from the plurality of ultrasonic wave transmission/reception elements to the subject; and
the processor is further configured to align the phase of the reception data by correcting the delay time based on the reception delay pattern selected.

12. A data processing method, comprising steps of:
transmitting an ultrasonic beam to a subject and receiving an ultrasonic echo, which is a reflected ultrasonic beam from the subject, to generate reception data;
correcting a delay time, which is a difference in arrival time of the ultrasonic echo in the reception data, to align a phase of the reception data;
setting two or more reception aperture levels of reception data which is used when producing an ultrasound image from reception data after correction of the delay time;
producing ultrasound images, the ultrasound images including an image for each of the corresponding set reception aperture levels by performing phase matching addition and a first data processing including at least one of correction of attenuation and gradation processing on the reception data after correction of the delay time corresponding to each of the set reception aperture levels; and
determining image qualities of the ultrasound images, the ultrasound images including an image for each of the corresponding set reception aperture levels and selecting at least an ultrasound image having an image quality equal to or greater than a first image quality from among the ultrasound images corresponding to the respective set reception aperture levels, the image quality including one of brightness, sharpness, or an index related to signal/noise.

13. The data processing method according to claim 12, further comprising a step of retaining the generated reception data in a reception data retention unit,
wherein the delay time of reception data read from the reception data retention unit is corrected to align the phase of the reception data.

14. The data processing method according to claim 12,
wherein ultrasound images corresponding to the respective set reception aperture levels are produced in parallel corresponding to all reception aperture levels of the reception data.

15. The data processing method according to claim 14,
wherein, after the phase of the reception data is aligned by correcting the delay time, the reception aperture levels of the reception data are set, and ultrasound images corresponding to the respective set reception aperture levels are produced in parallel.

16. The data processing method according to claim 14,
wherein, after the reception aperture levels of the reception data are set, the phase of the reception data is aligned by correcting the delay time corresponding to each of the set reception aperture levels, and ultrasound images corresponding to the respective set reception aperture levels are produced in parallel.

17. The data processing method according to claim 12,
wherein ultrasound images corresponding to the respective set reception aperture levels are sequentially produced using, in a time-division manner, a processor configured to produce an ultrasound image from the reception data.

* * * * *